United States Patent [19]
Berns et al.

[11] Patent Number: 5,913,874
[45] Date of Patent: Jun. 22, 1999

[54] CARTRIDGE FOR A SURGICAL INSTRUMENT

[75] Inventors: Mark I. Berns, Northbrook, Ill.; Dennis Reisdorf, Racine; Richard A. Booth, Jr., Milwaukee, both of Wis.

[73] Assignee: Cabot Technology Corporation, Wilmington, Del.

[21] Appl. No.: 08/937,837

[22] Filed: Sep. 25, 1997

[51] Int. Cl.$^6$ .................................................. A61B 17/28
[52] U.S. Cl. .............................................. 606/205; 606/51
[58] Field of Search .................................. 606/205, 170, 606/167, 206, 50–52

[56] References Cited

U.S. PATENT DOCUMENTS

| | | |
|---|---|---|
| 1,903,129 | 3/1933 | Peterson . |
| 3,938,527 | 2/1976 | Rioux et al. . |
| 4,016,881 | 4/1977 | Rioux et al. . |
| 4,499,898 | 2/1985 | Knepshield et al. . |
| 4,574,803 | 3/1986 | Storz . |
| 4,733,662 | 3/1988 | DeSatnick et al. . |
| 4,750,489 | 6/1988 | Berkman et al. . |
| 4,877,026 | 10/1989 | de Laforcade . |
| 4,985,030 | 1/1991 | Melzer et al. . |
| 5,036,860 | 8/1991 | Leigh et al. . |
| 5,224,951 | 7/1993 | Freitas . |
| 5,250,065 | 10/1993 | Clement et al. . |
| 5,258,005 | 11/1993 | Christian . |
| 5,258,006 | 11/1993 | Rydell et al. . |
| 5,269,780 | 12/1993 | Roos . |
| 5,273,519 | 12/1993 | Koros et al. . |
| 5,273,524 | 12/1993 | Fox et al. . |
| 5,314,424 | 5/1994 | Nicholas . |
| 5,334,198 | 8/1994 | Hart et al. . |
| 5,338,292 | 8/1994 | Clement et al. . |
| 5,342,359 | 8/1994 | Rydell . |
| 5,342,391 | 8/1994 | Foshee et al. . |
| 5,383,876 | 1/1995 | Nardella . |
| 5,403,312 | 4/1995 | Yates et al. . |
| 5,445,638 | 8/1995 | Rydell et al. . |
| 5,458,598 | 10/1995 | Feinberg et al. . |
| 5,486,185 | 1/1996 | Freitas et al. . |
| 5,499,997 | 3/1996 | Sharpe et al. . |
| 5,507,774 | 4/1996 | Holmes et al. . |
| 5,569,243 | 10/1996 | Kortenbach et al. . |
| 5,571,100 | 11/1996 | Goble et al. . |
| 5,611,808 | 3/1997 | Hossain et al. . |

Primary Examiner—Michael Buiz
Assistant Examiner—Kevin Truong
Attorney, Agent, or Firm—Austin R. Miller

[57] ABSTRACT

A cartridge for use in a medical instrument having a body and a sheath extending from the body. The preferred medical device has a housing, opposed tissue manipulators, and a tissue transecting blade mounted for reciprocal movement with respect to the housing and manipulators. The housing is mountable within the instrument's sheath for reciprocal sliding with respect to the sheath.

13 Claims, 4 Drawing Sheets

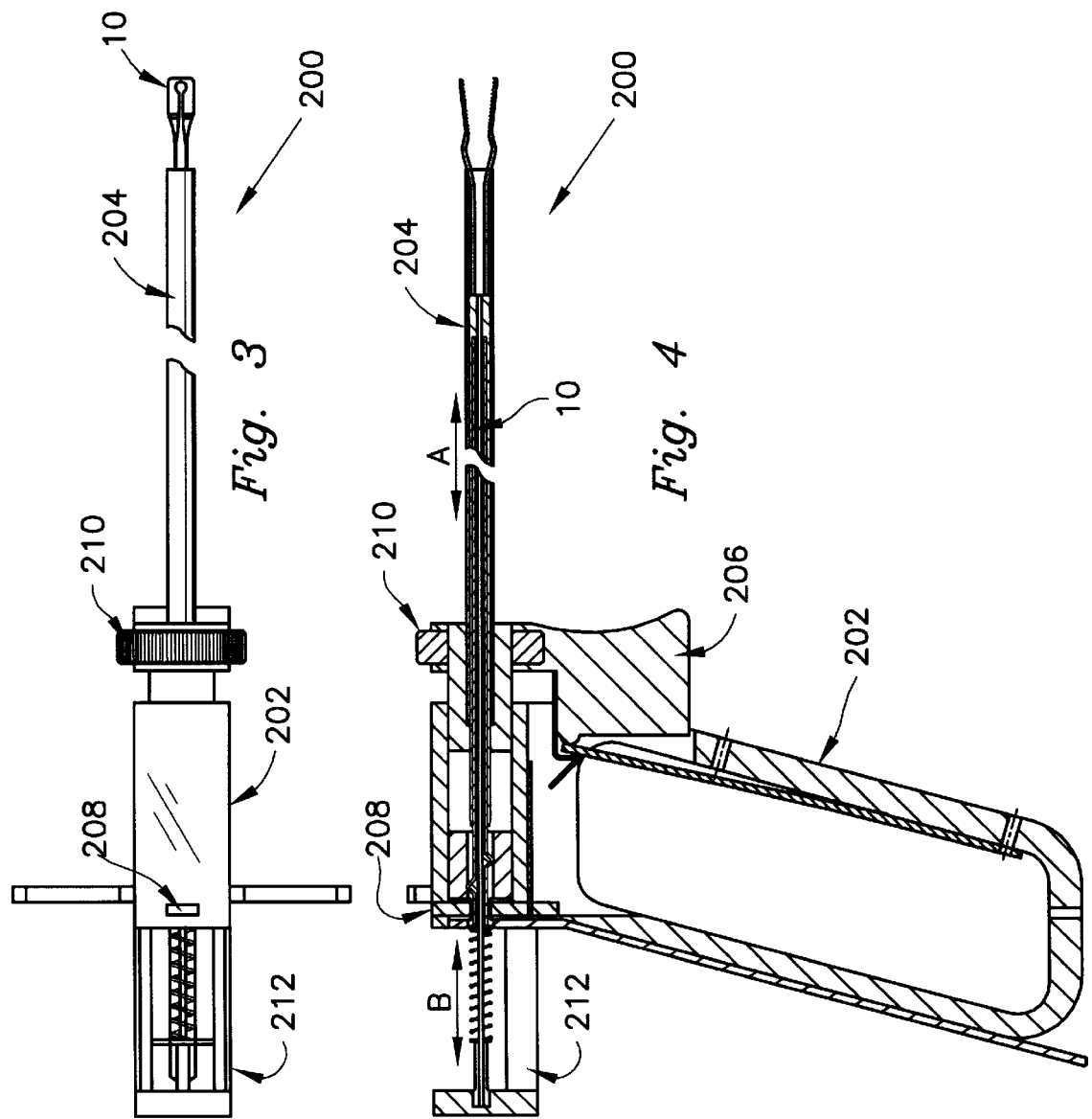

5,913,874

CARTRIDGE FOR A SURGICAL INSTRUMENT

BACKGROUND OF THE INVENTION

This invention relates to a tissue manipulating device for disposable or reusable surgical instruments. A preferred embodiment relates to a removable and replaceable cartridge for use in a reusable surgical instrument adapted for grasping, coagulating and transecting tissue.

FIELD OF THE INVENTION

The development of minimally invasive surgical procedures (such as endoscopic and laparoscopic procedures, for example) has created a great demand for surgical instruments for use during such procedures.

An example of an improved surgical device is described by Marc Feinberg et al. in U.S. Pat. No. 5,458,598 and U.S. Design Pat. No. 358,887 (both incorporated herein by reference) and is embodied in the SEITZINGER TRIPOLARO® Cutting Forceps available from Circon Cabot, 3037 Mt. Pleasant Street, Racine, Wis. 53404 (Circon Cabot Model No. 006689-901). The SEITZINGER TRIPOLAR® forceps instrument has a mechanical cutting blade and bipolar coagulating jaws. The bipolar jaws grasp tissue to be severed and a high-frequency voltage is applied across the jaws to coagulate the grasped tissue. Once coagulated, the tissue is mechanically cut by advancing the blade.

The SEITZINGER TRIPOLAR® forceps instrument is disposable. A new instrument is used for each surgical procedure to provide a clean and sharp blade. The used instrument is then discarded. Such a disposable instrument is highly desirable. However, there remains a need for surgical instruments that are reusable for multiple procedures to reduce the cost of the instrument per procedure.

Providing a reusable instrument presents unique challenges. For example, it may be necessary for the instrument to have a tissue manipulating device that is securely mounted to the instrument. On the other hand, a manipulating device adapted for a reusable instrument is preferably removable and replaceable between surgical procedures without requiring substantial disassembly of the reusable instrument or labor intensive procedures.

Jacques E. Rioux et al., in U.S. Pat. Nos. 3,938,527 and 4,016,881, describe a laparoscopic instrument with a disposable probe element. The Rioux probe element includes a sheath, electrodes, an electrode separator, and a heat shrink sleeve over the separator. A cutter can be fixedly mounted to the extremity of the sheath for cutting as the electrodes are drawn into the sleeve.

In U.S. Pat. No. 4,733,662, Allen H. DeSatnick et al. describe a disposable sheath and blade assembly for attachment to a reusable handle. The DeSatnick instrument includes a gripping blade slidably guided within the sheath parallel and immediately adjacent to a cutting blade. The gripping blade is used to engage tissue and the cutting blade is advanced to sever the gripped tissue.

A significant advance is described by K. Mossadeq Hossain et al. in U.S. Pat. No. 5,611,808. Like the instrument described by Feinberg et al. in U.S. Pat. No. 5,458,598, the Hossain instrument is adapted for grasping, coagulating and transecting tissue. The Hossain instrument differs in that it features a removable and replaceable blade.

Nevertheless, there remains a demand for an improved and economical reusable surgical instrument having a tissue manipulator that is securely mounted to the instrument during use, yet is easily removed and replaced between surgical procedures.

OBJECTS OF THE INVENTION

It is an object of this invention to provide an assembly adapted for use in a disposable or reusable surgical instrument that is securely mounted to the instrument during use.

Another object is to provide an assembly adapted for easy removal and replacement during or between surgical procedures.

Other objects will become clear to those of skill in this art in view of the following disclosure.

SUMMARY OF THE INVENTION

This invention provides a medical device, such as a removable and replaceable cartridge, that is adapted for use in a medical instrument. The preferred instrument is capable of grasping, coagulating, and transecting tissue during endoscopic procedures. The medical device is adapted for removal and replacement during or between procedures so that the remainder of the instrument can be reused for multiple procedures.

The medical device includes a housing that is sized for insertion into a sheath of the medical instrument. Opposed tissue manipulators such as tongs or jaws preferably extend longitudinally from a distal portion of the housing. Such manipulators can be adapted to grasp tissue, for example. A tissue transecting blade is preferably mounted for reciprocal longitudinal movement with respect to the housing and with respect to the opposed manipulators. The blade is preferably adapted to transect tissue that is grasped by the manipulators.

The housing of the medical device is mountable within the instrument's sheath so that it can reciprocate with respect to the sheath by movement of the housing or by movement of the sheath. Such reciprocal movement permits the control of the opposed manipulators.

The blade preferably includes an elongated portion that extends along the housing so that the blade can be manipulated during use. In a preferred embodiment, the blade is provided with a bias in a proximal direction, and a compression spring contacting the blade and the housing is preferably used to maintain the proximal bias.

If the medical instrument in which the medical device is intended to be used is adapted for electrocoagulation of tissue, then the medical device preferably includes conductors that extend longitudinally along the housing. Each of the conductors is electrically connected to a respective manipulator. The housing can also include an electrical barrier between the conductors so that they can remain electrically isolated from one another.

One of the opposed manipulators preferably includes a jaw portion that is positioned for grasping tissue during a surgical procedure. A longitudinally-extending recess is preferably provided in such a jaw to accommodate the blade so that at least a portion of the blade can be extended into the recess in order to cut grasped tissue.

A seal can be provided adjacent to an outer surface of the medical device's housing. Such a seal is useful to prevent any undesirable fluid flow between the housing's outer surface and the instrument sheath's interior surface when the housing is inserted into the sheath and the instrument is in use. For example, a close fit between the housing and the sheath can provide the seal. Alternatively, one or more O-ring seals or other known sealing systems can be provided at the outer surface of the housing to form a seal against the inside surface of the instrument's sheath.

BRIEF DESCRIPTION OF THE DRAWINGS

FIG. 3 is a top view of a medical instrument provided with a medical device according to the invention.

FIG. 4 is a cross-sectional side view of the medical device shown in FIG. 3.

DETAILED DESCRIPTION OF THE INVENTION

Figure 1:
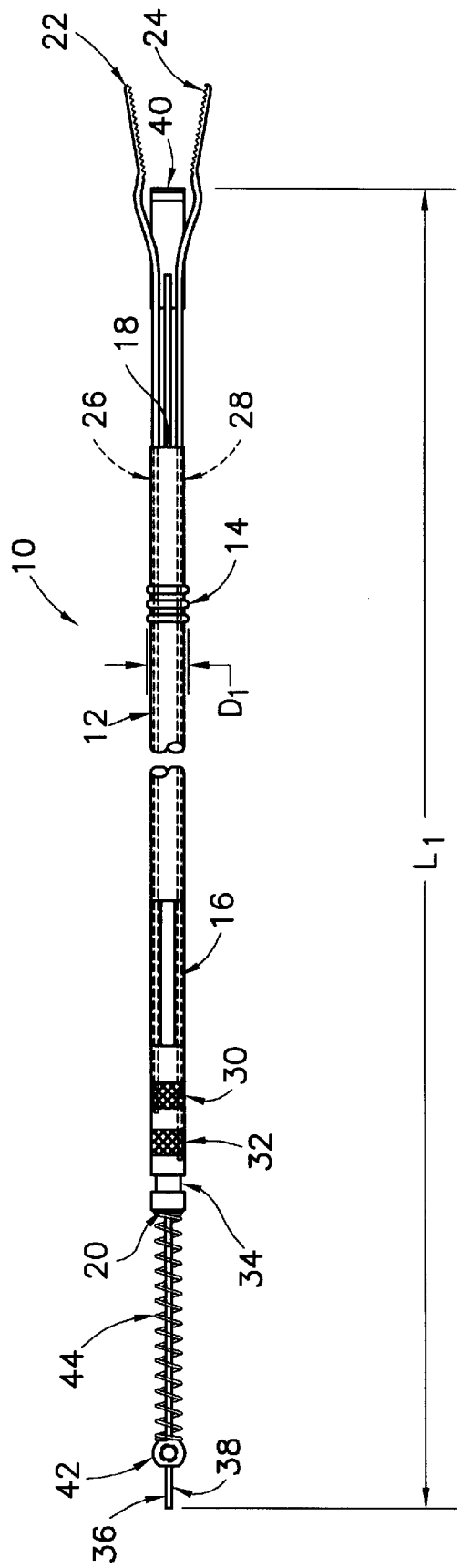
FIG. 1 is a side view of a medical device according to this invention.

The invention will now be described with reference to several medical device embodiments selected for illustration in the drawings. It will be appreciated that the spirit and scope of this invention is not limited to the embodiments shown in the drawings or the following description. Instead, the invention is defined separately in the appended claims. Also, it will be appreciated that the drawings are not necessarily to scale and that any reference to dimensions in the drawings or the following description are provided for illustrative purposes only and are not important to the invention.

Referring to FIG. 1, an embodiment of a cartridge according to this invention is generally designated by the numeral "10". Cartridge 10 is in the form of an insertable and removable cartridge that is intended for insertion into the sheath of a medical instrument (not shown in FIG. 1 but shown in FIGS. 3–5. The cartridge 10 provides components to grasp, coagulate, and transect tissue as necessary during a surgical procedure. Cartridge 10 is especially well-suited for use in an endoscopic instrument that is intended for insertion into an operative site through a small incision during a minimally invasive surgical procedure. Cartridge 10 is contemplated for use with other shapes and types of instruments and procedures as well.

In this embodiment, cartridge 10 desirably includes a cylinder 12 that extends along the majority of the length of cartridge 10. Cylinder 12 is preferably formed from a moldable plastic material, such as ABS, that is suited for medical applications. For reasons to be clarified later, cylinder 12 is most preferably formed from an insulating plastic material. Alternatively, cylinder 12 can include a metallic tube at its outer surface in order to make it rigid. Preferably, cylinder 12 is sized for a close fit within an instrument sheath to prevent gaseous or liquid fluid leakage through the sheath. Alternatively, a seal, such as the set of three O-rings 14 as shown in FIG. 1, can be provided on the outer surface of cartridge 12, or in grooves provided in the cartridge's surface in order to provide a means for sealing between the outer surface of cartridge 12 and an interior surface of a sheath (not shown in FIG. 1 but shown in FIGS. 4 and 5). O-rings 14, if used, are preferably formed from an elastomeric material that is compatible with medical and surgical applications. Although three O-rings 14 are illustrated, it is contemplated that fewer or more O-rings can be used, if at all, and that O-rings can be replaced with other known devices for forming a seal. Nevertheless, such O-rings 14 have an outer diameter $D_1$ (FIG. 1) that is slightly greater than the outer diameter of cylinder 12.

Cylinder 12 is provided with a series of flats 16 so that a portion of cylinder 12 is provided with a cross-sectional shape to permit engagement for rotation of cylinder 12 for insertion into and removel from an instrument sheath. For example, an octagonal cross-sectional shape can be provided. Flats 16 help provide a surface of cylinder 12 that can be engaged for rotation of the cylinder within an instrument's sheath. Such rotation may be desirable so that the instrument can manipulate tissue in a variety of directions and orientations.

Cylinder 12 has a distal end 18 and a proximal end 20. Extending from distal end 18 to proximal end 20 is a through-hole, the purpose of which will be made clear later with reference to the description of the knife assembly. Extending from the distal end 18 of housing 12 is a pair of opposed tissue manipulators 22 and 24, also referred to as tongs or jaws. As illustrated in FIG. 1, tongs 22 and 24 are bent so as to be biased in a radial, outward direction with respect to the longitudinal axis of the cylinder 12. Ramps formed on tongs 22 and 24 are intended for contact with the interior end portion of an instrument's sheath, as further described hereafter, so that movement of tongs 22 and 24 outwardly with respect to the end of the sheath, or retraction of the sheath away from the tongs, permits the tongs to move radially outwardly away from one another in accordance with their bias to do so. Such radial, outward movement of tongs 22 and 24 permits the release of tissue grasped therebetween. Upon retraction of tongs 22 and 24 back toward the instrument's sheath, or extension of the instrument's sheath toward the tongs, the ramps on the respective tongs contact the sheath and cause the tongs to move radially inwardly towards one another. Such radial, inward movement of tongs 22 and 24 causes the tongs to grasp tissue for tissue coagulation and subsequent transection, as will be further described.

Each tong 22, 24 is preferably formed from a loop of metallic material that extends from the housing 12. Further details of possible embodiments are described in U.S. Pat. Nos. 5,458,598 and 5,611,808.

Shown in phantom lines in FIG. 1 is a pair of conductors or as wires 26 and 28 that extend through a majority of the length of housing 12. Conductor 26 is electrically connected to tong 22 and conductor 28 is electrically connected to tong 24. Toward the proximal end 20 of cylinder 12, contacts, shown as metallic rings 30 and 32 are provided. Contact 30 is electrically connected to conductor 26 and contact 32 is electrically connected to conductor 28. In a preferred embodiment, contacts 30 and 32 are rings crimped to the outer surface of housing 12 or welded to the respective conductors 26 and 28 to form electrical contact surfaces that extend about the circumference of housing 12. Alternatively, conductors 26 and 28 can be provided with bends near their proximal ends that extend to the outer surface of housing 12, thereby facilitating electrical contact between the conductors 26 and 28 and the respective components within the medical instrument, with or without the use of contact rings.

Adjacent to the proximal end 20 of housing 12 is a radial channel 34 (FIG. 1) that extends about the housing circumference. Channel 34 provides a surface for releasable engagement of cylinder 12 in the body of a medical instrument as will further become apparent hereinafter.

Cylinder 10 also includes a knife assembly 36 with an overall length designated "$L_1$". Knife assembly 36 includes a knife rod 38 that extends through the through-hole formed in cylinder 12 and out from the proximal end 20 of cylinder 12. Connected to an opposite end of knife rod 38 is a knife blade 40 with a sharpened, tissue-cutting edge. Connected to knife assembly 36 toward a proximal end of knife rod 38 is a fastener 42 which can be attached by means of a set screw or an equivalent mechanical fastener. Knife blade 40 is most preferably biased toward the proximal direction so that release of a knife actuator such as a lever in the medical instrument will permit the knife to be withdrawn in the proximal direction and toward or into the sheath of the instrument. A compression spring 44 is preferably provided for contact between the proximal end 20 of cylinder 12 and a surface of fastener 42. Such a spring 44 pushes knife blade 40 in the proximal direction.

Figure 2:
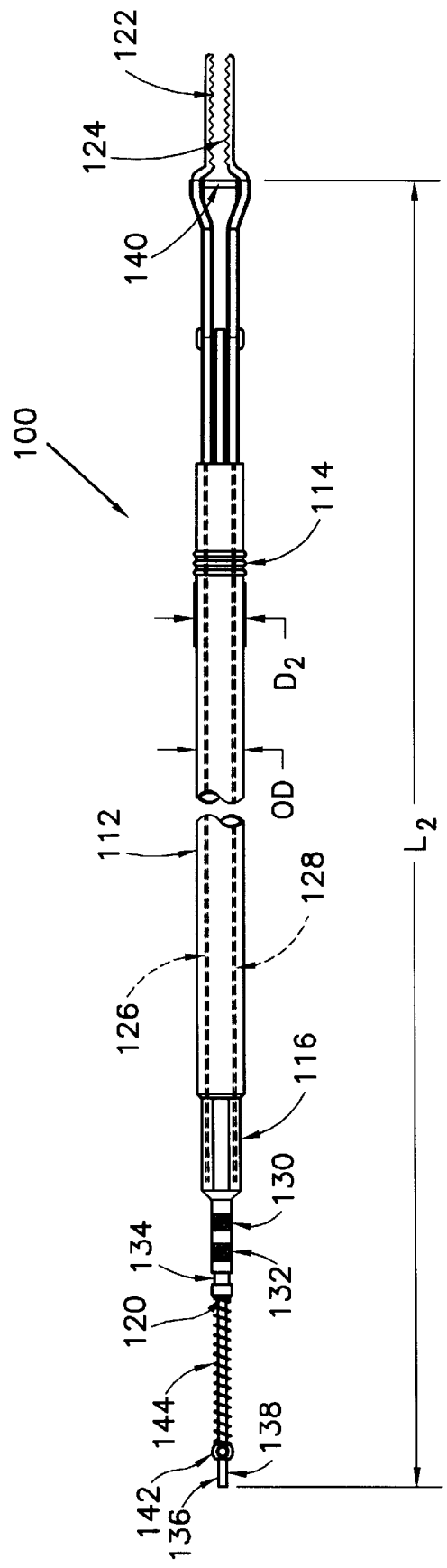
FIG. 2 is a side view of another embodiment of a medical device according to this invention.

Referring now to FIG. 2, another embodiment of a medical device or cylinder according to this invention is generally designated by the numeral "100". Revise 100 includes a molded cylinder 112 on which O-rings 114 can be mounted as before. Flats 116 are also provided on the housing's surface as before. Extending from a distal end of cylinder 112 are tongs 122 and 124, and conductors 126 and 128 (shown in phantom lines) extend for connection to tongs 122 and 124, respectively. Toward a proximal end 120 of cylinder 112 are contacts 130 and 132 connected to conductors 126 and 128, respectively. Also adjacent to proximal end 120 is a radial channel 134, as before, to facilitate the releasable engagement of medical device 100 in the medical instrument. Device 100 also includes a knife assembly 136 having a knife rod 138 and a knife blade 140. Knife assembly 136 has an overall length designated "$L_2$". Knife rod 138 extends through a through-hole that extends between the distal end 118 and proximal end 120. A spring 144 is provided between a fastener 142 on the knife assembly 136 and proximal end 120 in order to bias the knife blade 140 in a proximal direction, all as before.

Cylinder device 100 differs from device 10 primarily in that it is adapted for use in a surgical instrument having a sheath with a larger inner diameter. It will be appreciated that the taper provided between octagonal flats 116 and contact 130 provides a transition between a smaller proximal portion and the larger diameter portion of housing 112 which has an outer diameter labeled "OD" in FIG. 2. Also, O-rings 114 of device 100, if used, have an outer diameter $D_2$ which is slightly greater than outside diameter OD. However, cylinder 112 is preferably sized for a close fit in the instrument sheath to provide an at least partial seal against gas or liquid flow without a separate seal component. It will be appreciated that a medical device according to this invention can be provided with any outer diameter so that it can be used within the sheath of a wide variety of instruments in a wide variety of applications. Also, such a taper makes it possible to provide an enlarged medical device 100 with a smaller diameter proximal end portion. Such a configuration facilitates the use of common instrument components to accommodate medical devices for various sheath sizes.

Referring now to FIGS. 3 and 4, an installation of a medical device according to this invention in a surgical instrument will be described. For purposes of illustration, cylinder 10 is shown mounted in a medical instrument generally designated by the numeral "200". Instrument 200 is a reusable or disposable instrument adapted to perform grasping, coagulating, and transecting functions in the course of laparoscopic surgical procedures. Instrument 200 can be provided in a wide variety of configurations and materials, depending upon manufacturer preference and consumer needs. Instrument 200 has a body 202 that forms a handle shaped to be grasped by the user of the instrument. Extending from the body 202 is an instrument sheath 204 that is substantially tubular in construction. Body 202 of instrument 200 also includes a trigger mechanism 206 that is intended for manipulation by the finger of the instrument's user. Trigger 206 is connected to sheath 204 so that the activation of the trigger retracts sheath 204 toward the body 202 of instrument 200 and the release of trigger 206 causes the extension of sheath 204 outwardly away from the body. A spring mechanism in body 202 biases sheath 204 and trigger 206 in the extended position. A similar effect could also be accomplished by mounting medical device 10 in a movable receptacle connector so that the trigger causes the device 10 to move forward or backward with respect to a stationary sheath in order to open the manipulators or close the manipulators, respectively.

As shown in FIGS. 3 and 4, cylinder 10 can be inserted lengthwise to extend through the sheath 204 of instrument 200. A lock 208 is provided on body 202 in order to releasably mount or engage medical device 10 within the body and sheath of instrument 200. More specifically, lock 208 is positioned to engage medical device 10 at recess 34, for example. Such a lock holds the medical device or cylinder so that it cannot move along its axis with respect to the instrument's body.

As will be appreciated from the cross-sectional view shown in FIG. 4, actuation and release of trigger 206 causes movement of sheath 204 lengthwise as indicated by the arrow "A". Such manipulation of sheath 204 controls the jams of medical device 10. Specifically, actuation of trigger 206 to retract sheath 204 inwardly into the body of the instrument permits the manipulators to came the jams to expand radially outwardly away from one another as a result of their bias to do so. This can release grasped tissue. Conversely, release of trigger 206 causes sheath 204 to extend outwardly away from body 202. This causes the manipulators to close toward one another to grasp tissiue.

Attached to trigger portion 206 of body 202 is a rotary wheel 210 which engages flats such as flats 16 on medical device 10. Rotation of rotary wheel 210 by a user of instrument 200 causes rotation of medical device 10 within the sheath 204, thereby permitting alignment and orientation of the jaw-manipulators in a selected position. Connected to the proximal portion of body 202 and to the proximal portion of knife assembly 36 of medical device 10 is a pusher mechanism 212 that is movable in the directions designated "B" in FIG. 4. Pusher 212 can be manipulated by the user of the instrument 200, perhaps by thumb pressure, in order to advance the blade of the medical device. Specifically, compression of pusher 212 to a degree sufficient to compress spring 44 causes knife assembly 36 to be longitudinally advanced with respect to the remainder of medical device 10. Release of pusher 212 permits compression spring 44 to bias the knife assembly 36 into the proximal direction.

Medical device 10 is preferably installed into medical instrument 200 by inserting it, proximal end first, into the open distal end of sheath 204 until the proximal end of knife assembly 36 contacts pusher 212 and radial channel 34 becomes substantially aligned with lock 208. Upon actuation of lock 208, medical instrument 200 is ready for use.

Subsequent to the use of medical instrument 200 during a surgical procedure, medical device 10 is released from body 202 by releasing the lock 208. The medical device 10 can then be removed from medical instrument 200 outwardly through the distal end of sheath 204 and discarded when so desired.

Figure 5:
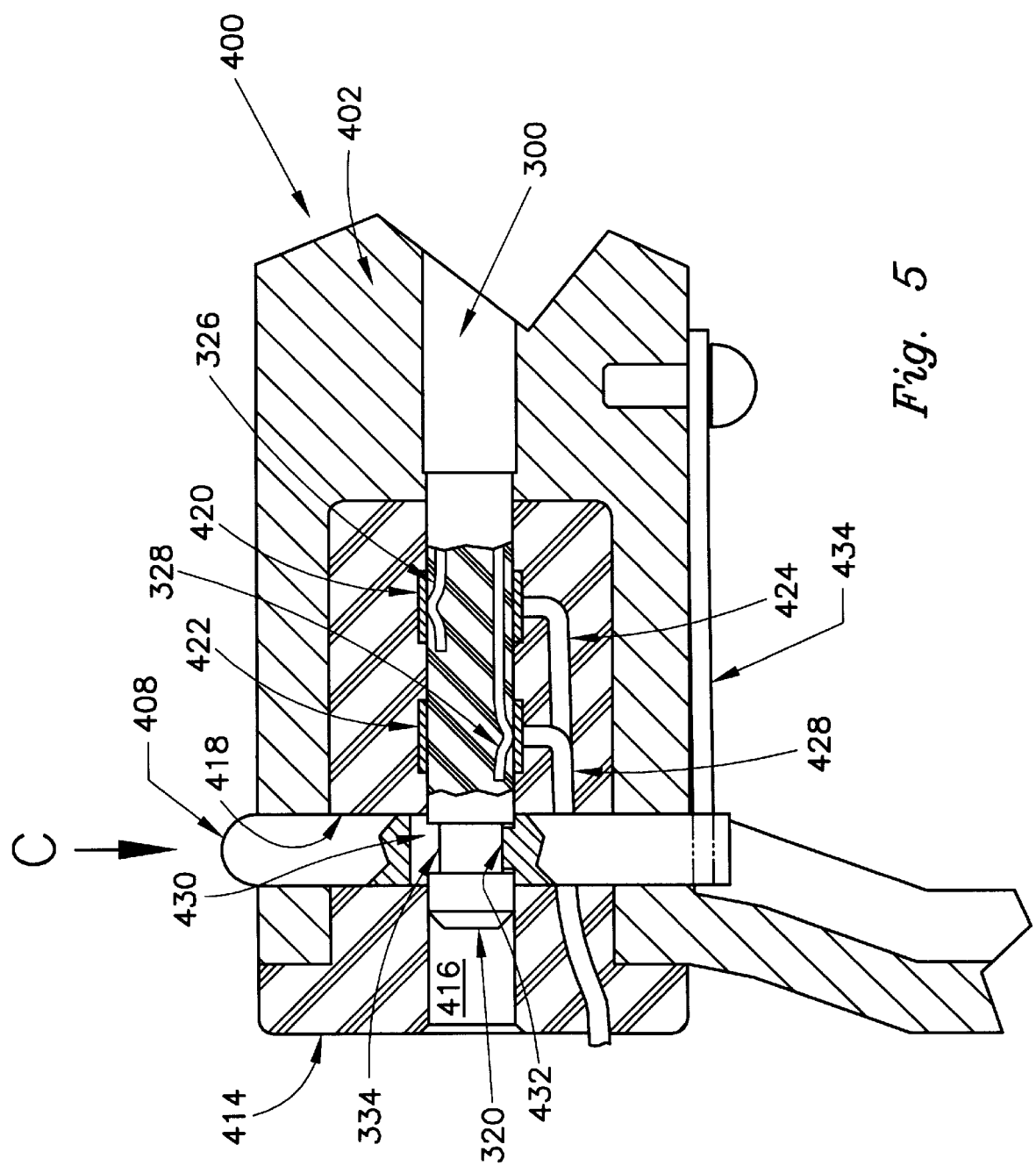
FIG. 5 is a cross-sectional side view of a detail of a medical instrument provided with a medical device according to the invention.

Referring now to FIG. 5, details of an embodiment of a medical device or cartridge "300" installed in an embodiment of a medical instrument "400" are shown for illustrative purposes. Medical device 300 is similar to devices 10 and 100 in that it includes a channel or recess 334 adjacent to a proximal end 320. It also includes a pair of conductors 326 and 328 provided for electrical connection of opposed manipulators (not shown). It can be seen that each conductor 326 and 328 includes an outwardly extending bend that extends to an outer surface of the housing of device 300. However, device 300 does not include contact components corresponding to rings 30 and 32 of device 10 or rings 130 and 132 of device 100. Instead, conductors 326 and 328 are positioned for electrical contact with contacts provided in instrument 400, as will be described.

In this embodiment, instrument 400 includes a body portion 402. Mounted in body 402 is a locking/release pin 408 (similar to lock 208 of instrument 200) and a receptacle 414. Pin 408 and receptacle 414 can be molded from ABS or formed in any other known manner from other suitable materials. Receptacle 414 can have a circular, rectangular or other cross-sectional shape depending on the manner in which it is to be mounted in the body 402. Also, it can be mounted for stationary engagement in body 402 (e.g. in embodiments wherein device 300 remains stationary with respect to body 402 during use and the instrument's sheath is moved to open and close manipulators) or it may be mounted for longitudinal reciprocal movement within body 402 (e.g. in embodiments wherein device 300 is reciprocated within a stationary sheath to open and close manipulators). Extending through receptacle 414 is defined a passageway 416 sized and positioned to receive a proximal end portion of device 300. Also defined in receptacle 414 is a slot 418 sized and positioned to receive locking/release pin 408. Mounted within receptacle 414 adjacent to passageway 416 are two ring-shaped contacts 420 and 422. Contacts 420 and 422 are preferably formed from steel or brass rings, but other electrically conductive materials can be used. Contact 420 is positioned for electrical contact with conductor 326 of device 300 and contact 422 is positioned for electrical contact with conductor 328. Electrically connected to contracts 420 and 422 are receptacle conductors 424 and 428, respectively, which extend from contacts 420 and 422 and out from receptacle 414 to an external power supply (not shown). Contacts 420 and 422 and conductors 424 and 428 can be molded into a molded receptacle 414 or can be formed and installed in any other known manner.

Locking/release pin 408 is mounted for vertical sliding within slot 418 of receptacle 414. It defines an opening 430 through which the proximal portion of device 300 can be inserted or retracted. It also defines a detent or rib 432 sized to fit within channel 334 of device 300 to releasably engage the device and prevent its longitudinal removal from receptacle 414 and body 402 of instrument 400. Attached to a portion of instrument body 402 is a spring wire or strip 434 that is positioned to engage a bottom portion of locking/release pin 408 and to bias the pin in the upward direction so that rib 432 engages channel 334.

In operation, device 300 is installed into instrument 400 by pressing pin 408 downwardly in the direction designated "C" and inserting the proximal portion of device 300, proximal end first, into passageway 416 of receptacle 414 and through opening 430 in pin 408 until channel 334 of device 300 is axially aligned with rib 432. Pin 408 is then released so that spring 434 can urge pin 408 upwardly until rib 432 engages channel 334. In this installed position, conductors 326 and 328 are axially aligned for electrical connection with contacts 420 and 422, respectively.

The instrument 400, together with device 300, is then ready for use to perform a surgical procedure. After such use, device 300 can be removed from instrument 400 by again pressing pin 408 downwardly in direction "C" and removing the proximal portion of device 300 from passageway 416 and opening 430 until it is entirely separated from instrument 400. Instrument 400 is then poised to receive a new device or reinsertion of device 300.

It is contemplated that many modifications can be made to the medical device embodiments selected for illustration in the drawings. For example, although housings 12 and 112 are preferably molded, they can be formed from a hollow structure such as a plastic or metallic tube through which electrically-insulated conductors and the knife rod can extend. Also, electrical connection to the tongs can be made by simply extending the tongs through the housing toward the housing's proximal end.

Many other modifications can be made to the specific embodiments shown in the Figures without departing from the spirit and scope of this invention. The configuration, materials and shapes of the components of the specific embodiments disclosed are optionally modified or replaced, depending upon specific intended uses of the surgical instrument and manufacturer preferences. For example, the manipulating portion shown in the Figures can be replaced with any tool (or group of tools) that is intended to be replaced or interchanged, yet is intended to be mounted securely within the instrument during use. For example, the manipulating portion optionally includes an electrode; a tissue manipulating tool; a stapler mechanism; tools that are difficult to sterilize; tools that are only effective for a single use or only a few uses; or any other tool wherein removal and replacement of that tool, periodically or between each surgical procedure, benefits the overall effectiveness of the surgical instrument.

In any embodiment, the medical device according to this invention confers significant benefits. It provides a cost-effective cartridge or sub-assembly that can be easily inserted into a reusable surgical instrument. During use the medical device is securely engaged and controlled by the surgical instrument. After a surgical procedure is completed, the medical device can be easily removed and replaced so that the surgical instrument can be reused for numerous procedures, each time with a new and sterile device. Accordingly, the medical device of this invention can be used to reduce the instrument cost per procedure without compromising the quality or performance of the instrument.

What is claimed is:

1. A detachable cartridge for sealable insertion into and removal from an actuating instrument having a body having a sheath that is shaped for detachable reception of said cartridge, said cartridge comprising:

a housing that is sized and shaped for insertion into said sheath of said actuating instrument;

a pair of spaced electrocautery jaws carried in said housing and extending longitudinally proximally from a distal portion of said housing; and a cutting blade mounted at least partially within said housing and also extending longitudinally proximally from said distal end of said housing for reciprocal longitudinal movement along said housing and between said jaws;

releasable attaching and releasing means at said housing and releasably connectable to said sheath, wherein said housing is sealably mountable and connectable within said sheath for driveable connection for relative longitudinal movement of said housing with respect to said sheath, and control means attached to said actuating instrument for control of movement of said electrocautery jaws and said cutting blade of said cartridge during use of said cartridge.

2. The cartridge defined in claim 1, wherein said cutting blade is provided with a bias toward a proximal direction with respect to said housing.

3. The cartridge defined in claim 1, wherein said cutting blade is mounted for reciprocal longitudinal movement influenced by said body, over an axial distance with respect to said housing, said movement being independent of said housing.

4. The cartridge defined in claim 1, wherein said cartridge further comprises conductors extending longitudinally along said housing, each of said conductors being electrically connected to a respective one of said jaws.

5. The cartridge defined in claim 4, wherein said housing has an electrical barrier between said conductors.

6. The cartridge defined in claim 1, wherein at least one of said jaws defines a longitudinally extending recess, and wherein a portion of said cutting blade extends into said recess.

7. The cartridge defined in claim 1, further comprising a seal positioned adjacent to an outer surface of said housing to resist liquid or gaseous fluid flow between said outer surface of said housing and an interior surface of said sheath when said housing is inserted into said interior of said sheath.

8. The cartridge defined in claim 1, wherein said housing is also releasably mountable for relative rotational movement of said housing with respect to said sheath.

9. A detachable cartridge for use in combination with a cutting and coagulating forceps having a connecting sheath shaped for connection with said cartridge, said forceps being adapted for actuating electrocoagulation and cutting of tissue in combination with said cartridge, said cartridge being constructed for sealable insertion into, and actuable connection with said sheath, and for subsequent removal therefrom, said cartridge comprising:

a tubular housing that is sized and shaped for insertion into said sheath of said forceps, said housing comprising tubing having a distal end opening;

opposed tissue electrocautery jaws openable and closeable beyond said open end of said tubing and extending longitudinally from a distal portion of said tubing toward its proximal end;

a plurality of conductors extending longitudinally within said housing, each of said conductors being electrically connected to a different one of said opposed electrocautery jaws;

said tubing being provided with an electrical barrier between said conductors;

a tissue transecting blade mounted at least partially within said tubular housing for reciprocal longitudinal movement back and forth with respect to said housing and said electrocautery jaws, said tissue transecting blade comprising an elongated portion extending along said housing to said proximal end portion of said tubing for actuating movement of said tissue transecting blade in the direction of its axis; and connecting means for sealably and releasably mounting said tubing to extend within said sheath of said forceps for relative reciprocal longitudinal movement of said tubing with respect to said sheath for manipulating said jaws during use of said forceps when connected to said detachable cartridge, and for removal of said cartridge from said forceps after use.

10. The cartridge defined in claim 9, wherein said cutting blade is provided with a bias toward a proximal direction with respect to said housing.

11. The cartridge defined in claim 10, further comprising a spring contacting said blade and said housing to provide said bias.

12. The cartridge defined in claim 9, further comprising a seal positioned adjacent to an outer surface of said housing to resist liquid or gaseous fluid flow between said outer surface of said housing and an interior surface of said sheath when said housing is inserted into said interior of said sheath.

13. The cartridge defined in claim 9, wherein said housing is also releasably mountable for relative rotational movement of said housing with respect to said sheath.

* * * * *

UNITED STATES PATENT AND TRADEMARK OFFICE
CERTIFICATE OF CORRECTION

PATENT NO. : 5,913,874
DATED : June 22, 1999
INVENTOR(S) : Berns et al.

It is certified that error appears in the above-identified patent and that said Letters Patent is hereby corrected as shown below:

In column 10, Claim 9, at approximately line 2, please change "open end" to -- distal end opening -- .

Signed and Sealed this

Twenty-sixth Day of December, 2000

*Attest:*

Q. TODD DICKINSON

*Attesting Officer*      *Director of Patents and Trademarks*